(12) United States Patent
Hirano

(10) Patent No.: US 9,967,643 B2
(45) Date of Patent: May 8, 2018

(54) EARPHONE

(71) Applicant: KYOCERA Corporation, Kyoto (JP)

(72) Inventor: Asao Hirano, Koganei (JP)

(73) Assignee: KYOCERA Corporation, Kyoto (JP)

( * ) Notice: Subject to any disclaimer, the term of this patent is extended or adjusted under 35 U.S.C. 154(b) by 0 days. days.

(21) Appl. No.: 15/305,052

(22) PCT Filed: Apr. 21, 2015

(86) PCT No.: PCT/JP2015/002173
§ 371 (c)(1),
(2) Date: Oct. 18, 2016

(87) PCT Pub. No.: WO2015/162913
PCT Pub. Date: Oct. 29, 2015

(65) Prior Publication Data
US 2017/0188126 A1 Jun. 29, 2017

(30) Foreign Application Priority Data

Apr. 22, 2014 (JP) .................................. 2014-088113

(51) Int. Cl.
*H04R 1/10* (2006.01)
*H04R 17/00* (2006.01)

(52) U.S. Cl.
CPC .......... *H04R 1/1016* (2013.01); *H04R 1/105* (2013.01); *H04R 1/1058* (2013.01);
(Continued)

(58) Field of Classification Search
CPC .... H04R 1/1016; H04R 1/105; H04R 1/1058; H04R 1/1066; H04R 1/1075;
(Continued)

(56) References Cited

U.S. PATENT DOCUMENTS 1,576,938 A * 3/1926 Struxiano .............. H04R 1/105
381/328
8,712,087 B2 4/2014 Ozawa
(Continued)

FOREIGN PATENT DOCUMENTS

JP 2004-208220 A 7/2004
JP 2008-177705 A 7/2008
(Continued)

OTHER PUBLICATIONS

International Search Report issued in PCT/JP2015/002173; dated Jun. 9, 2015.
(Continued)

*Primary Examiner* — Joshua Kaufman
(74) *Attorney, Agent, or Firm* — Studebaker & Brackett PC

(57) ABSTRACT

An earphone (1) includes a cylindrical barrel (2) having one end thereof inserted in an ear canal, a transmission element (4) that is provided on a part of the side of the barrel (2), has a part thereof being in contact with a tragus of a human body while the barrel (2) is inserted in the ear canal and has a built-in electroacoustic conversion element (3) configured to generate an acoustic vibration in response to an electrical signal, a vibration element (5) that is provided on an inner wall of the barrel (2) and vibrates in reaction to the acoustic vibration from the electroacoustic conversion element (3), and a biosensor (30).

10 Claims, 15 Drawing Sheets

(52) U.S. Cl.
CPC ......... *H04R 1/1066* (2013.01); *H04R 1/1075* (2013.01); *H04R 1/1091* (2013.01); *H04R 17/005* (2013.01); *H04R 2201/10* (2013.01)

(58) Field of Classification Search
CPC .... H04R 1/1091; H04R 17/00; H04R 17/005; H04R 17/02; H04R 17/025; H04R 25/64; H04R 25/652; H04R 2201/10; H04R 2201/105

See application file for complete search history.

(56) References Cited

U.S. PATENT DOCUMENTS

| | | | |
|---|---|---|---|
| 2010/0292588 A1* | 11/2010 | Uenishi | A61B 5/02208 600/499 |
| 2012/0076341 A1 | 3/2012 | Ozawa | |
| 2015/0319521 A1* | 11/2015 | Yuen | H04R 1/1058 381/380 |
| 2016/0248894 A1* | 8/2016 | Hosoi | H04M 1/03 |

FOREIGN PATENT DOCUMENTS

| | | |
|---|---|---|
| JP | 2014-33405 A | 2/2014 |
| WO | 2010/134313 A1 | 5/2010 |
| WO | 2011/024425 A1 | 3/2011 |

OTHER PUBLICATIONS

Written Opinion issued in PCT/JP2015/002173; dated Jun. 9, 2015; with English language Concise Explanation.

\* cited by examiner

EARPHONE

CROSS-REFERENCE TO RELATED APPLICATIONS

This application claims priority to and the benefit of Japanese Patent Application No. 2014-088113 filed on Apr. 22, 2014, the entire contents of which are incorporated herein by reference.

TECHNICAL FIELD

This disclosure relates to an earphone that causes an eardrum and a tragus to vibrate.

BACKGROUND

As a type of earphone, an bone conduction type earphone has been proposed in which sound vibrates the skull and stimulates the inner ear such as cochlea or the like, vibrations are converted into electrical signals by the cochlea and the electrical signals are transmitted to the brain. An earphone equipped with a biosensor has been also proposed. For example, the user inserts an earphone into his/her ear to measure the pulse rate by using a biosensor.

SUMMARY

An earphone according to one embodiment of this disclosure to achieve the above mentioned purpose includes: a tubular barrel comprising one end thereof inserted in an ear canal, a transmission element that is provided on a part of the side of the barrel, has a part thereof being in contact with a tragus while the barrel is inserted in the ear canal and has a built-in electroacoustic conversion element configured to generate an acoustic vibration in response to an electrical signal, a vibration element that is provided on an inner wall of the barrel and configured to vibrate in reaction to the acoustic vibration from the electroacoustic conversion element and a biosensor.

DETAILED DESCRIPTION

Figure 1:
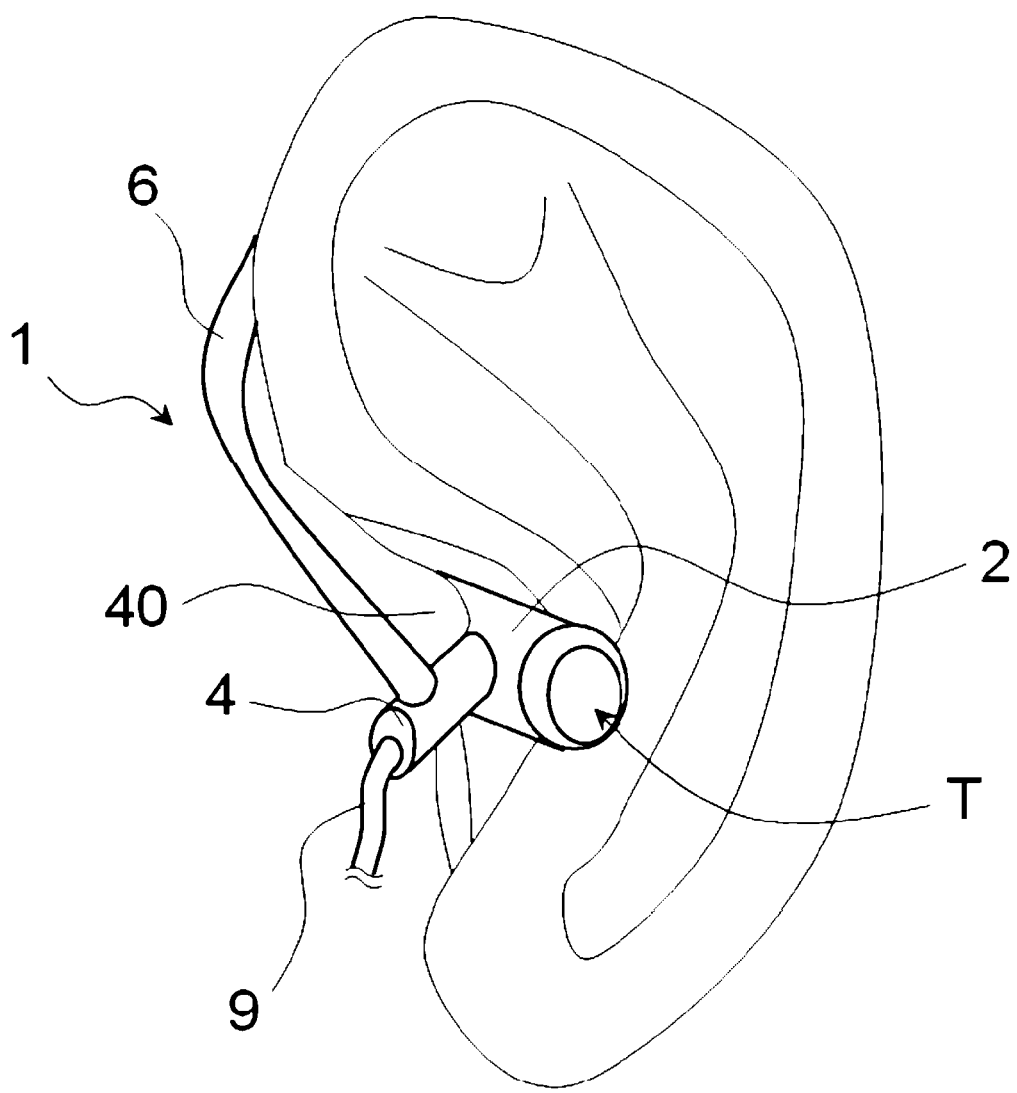
FIG. 1 is a schematic diagram illustrating a state where an earphone according to this embodiment is placed in the left ear.
Figure 2:
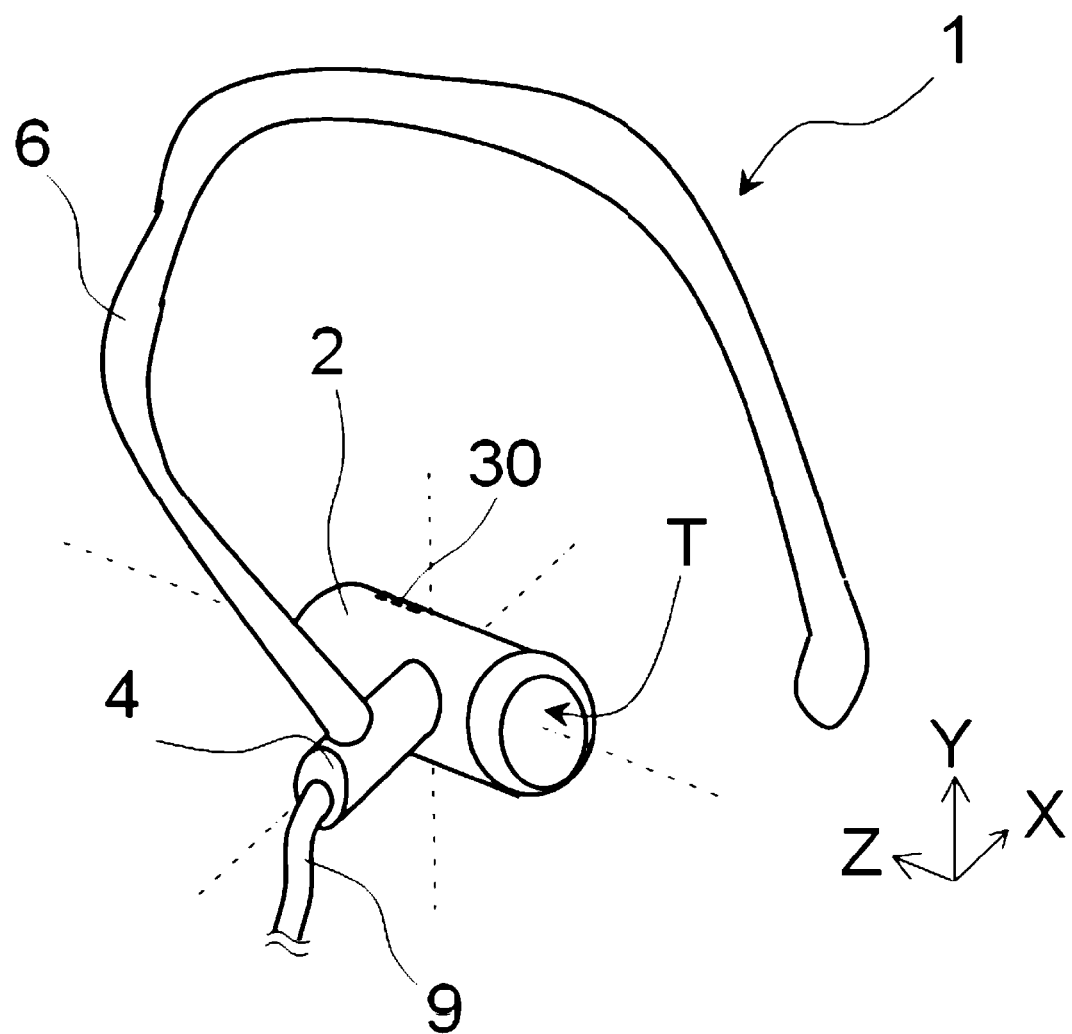
FIG. 2 is a schematic diagram illustrating the earphone according to this embodiment.

The following describes embodiments of an earphone according to this disclosure with reference to the attached drawings. It should be noted that this disclosure is not limited to the following embodiment, and FIGS. 1 to 4 illustrate an earphone that is attached to the left ear when used.

If the measuring object site of the biological information and the position of the biosensor vary, noise will be included in the biological information measured by using a sensor, which makes accurate measurement of the biological information difficult.

I therefore provide an earphone capable of improving the measurement accuracy of the biological information.

Since the vibration element is not disposed in the vicinity of the surface of the ear canal, the measuring object site of the biological information and the position of the biosensor are less likely to be fluctuated, and as a result, the measurement accuracy of the biological information can be improved.

Earphone Structure

The earphone 1 according to this embodiment is used to a portable music terminal such as, for example, a smartphone, a portable audio player, a portable media player or the like and a wireless communication terminal such as a radio or the like. The earphone 1 is placed in the ear when used. The earphone 1 has a cylindrical barrel 2 having one end thereof inserted into the ear canal of the human body, a transmission element 4 that is provided on a part of the side of the barrel 2, has a part thereof being in contact with a tragus 40 of the human body while the barrel 2 is inserted in the ear canal, and has a built-in electroacoustic conversion element 3 configured to generate an acoustic vibration in response to an electrical signal, and a vibration element 5 that is provided on an inner wall of the barrel 2 and configured to vibrate in reaction to the acoustic vibration from the electroacoustic conversion element 3. Furthermore, the transmission element 4 is provided with an elastically deformable hooking element 6 that is hooked to the auricle of the human body. The biosensor 30 is provided on a part of the barrel 2. The biosensor 30 is provided on the face that faces the surface of the ear canal while the barrel 2 is inserted in the ear canal.

The barrel 2 is cylindrical and is used by fitting into the ear canal. The barrel 2 is provided with a through port T. When the barrel 2 is fit into the ear canal, the space inside of the ear canal and the space outside of the ear canal are connected by the through port T.

Figure 3:
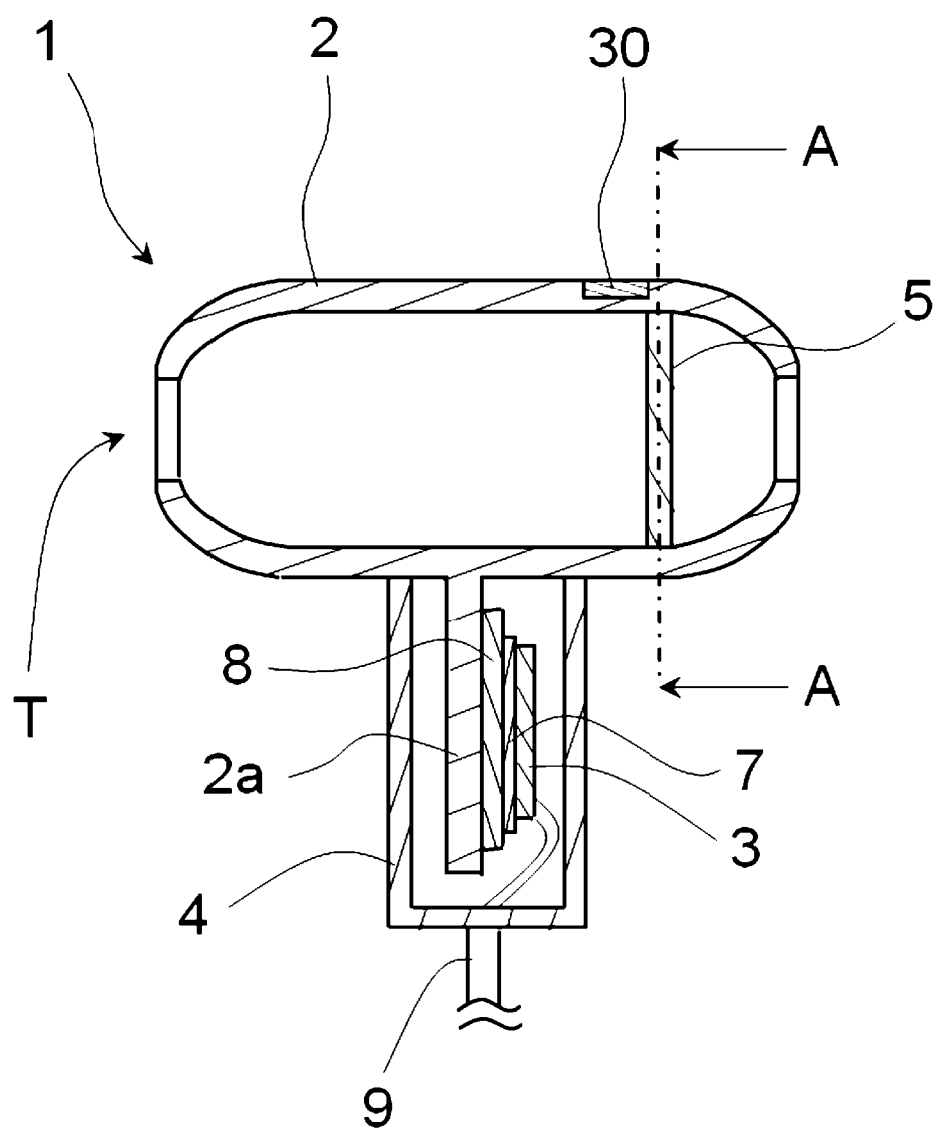
FIG. 3 is a cross-sectional view of the earphone of FIG. 2 in XZ plane.
Figure 4:
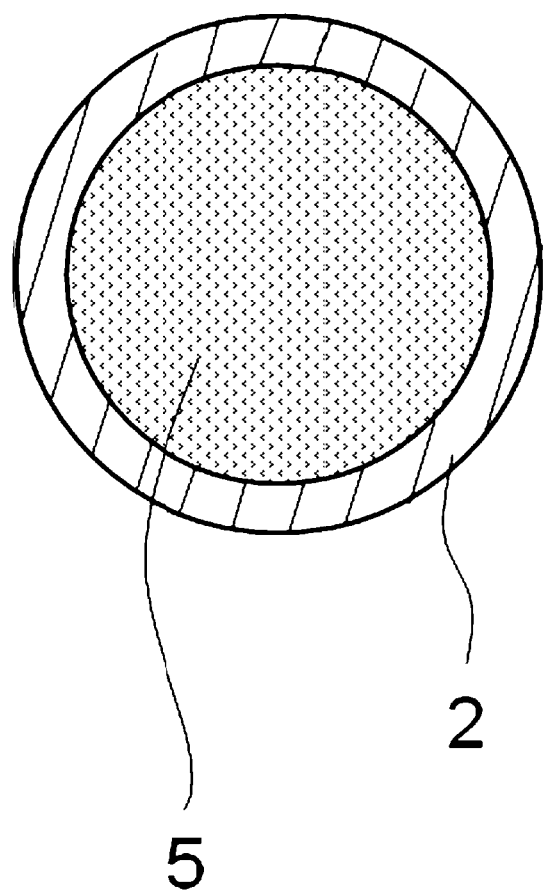
FIG. 4 is a cross-sectional view of a fitting element and a vibration element viewed along A-A in FIG. 3.

The barrel 2 is formed of a deformable elastic body, and thus can be deformed easily by a human force to fit into the ear canal. As illustrated in FIG. 3, both ends of the barrel 2 are curved to allow for easy fitting to the ear canal and are adjusted to prevent the inner wall of the ear canal from being damaged. Moreover, the barrel 2 is formed so that the outer diameter of each of both ends is smaller than that of the region sandwiched between the both ends. Reduction in the outer diameter of each of the both ends of the barrel 2 allows for easy fitting of one end of the barrel 2 into the ear canal. Furthermore, it is preferable that a part having the smallest outer diameter is formed between one end and the other end of the barrel 2. Although the ear canal is formed so that it reaches the eardrum through its complicated curve, provision of a part having the smallest outer diameter between the one end and the other end of the barrel 2 allows for easy fitting corresponding to the complicated shape of the ear canal.

The barrel 2 is elastically deformable, and is formed of resin such as, for example, epoxy resin, acrylic resin, silicon, urethane rubber or the like. The cylindrical outer diameter of the barrel 2 is set to 10 mm or more and 20 mm or less and the inner diameter thereof is set to 3 mm or more and 15 mm or less. The vertical length of the barrel 2 is set to 5 mm or more and 30 mm or less.

The barrel 2 has an extension 2a extending from the side of the barrel 2 to the direction orthogonal to the cylindrical axis of the barrel 2. The extension 2a is provided with the electroacoustic conversion element 3 via the joining element 7. Here, the cylindrical axis of the barrel 2 is coaxial to the axial direction of the through port T. It should be noted that the extension 2a may be separated from the barrel 2. In such case, the extension 2a is connected to the side of the barrel 2 via adhesive composed of, for example, epoxy resin, acrylic resin, silicon, urethane rubber or the like.

The extension 2a is in the form of a rectangular plate. A vibrator 8 is provided on the extension 2a. The extension 2a can be formed preferably by using a material such as, for example, synthetic resin having a large rigidity and elasticity. The acoustic vibration of the electroacoustic conversion element 3 is transmitted to the extension 2a via the vibrator 8 and can vibrate the transmission element 4 entirely. It should be noted that the extension 2a is formed of insulated material such as, for example, epoxy resin, acrylic resin, silicon, urethane rubber or the like. The extension 2a is also in the form of a plate, and is formed, for example, to have a length of a side of 20 mm or more and 80 mm or less and a thickness of 1.5 mm or more and 10 mm or less, for example.

The vibrator 8 is in the form of a rectangular plate. The vibrator 8 can be formed by preferably using a material having a large rigidity and elasticity such as, for example, acrylic resin, glass or the like. The vibrator 8 is provided on the extension 2a, and the lower surface of the vibrator 8 and the upper surface of the extension 2a are connected via adhesive material composed of, for example, epoxy resin, acrylic resin, silicone, urethane rubber or the like. It should be noted that the vibrator 8 is formed to have a length of a side of 5 mm or more and 60 mm or less and a thickness of 1 mm or more and 5 mm or less, for example.

The electroacoustic conversion element 3 is formed of a piezoelectric body having a bimorph structure. The electroacoustic conversion element 3 is formed by alternately laminating a plurality of polarized piezoelectric body layers and a plurality of electrode layers. The electroacoustic conversion element 3 vibrates to allow one principal surface and the other principal surface to be bent to generate acoustic vibrations. The electroacoustic conversion element 3 is also set in the rectangular parallelepiped shape having a length of 10 mm or more and 40 mm or less, a width of 1 mm or more and 30 mm or less, and a thickness of 0.3 mm or more and 5 mm or less, for example.

It should be noted that the piezoelectric body layer forming the electroacoustic conversion element 3 is formed of, for example, lead zirconate, lead zirconate titanate, and lead-free piezoelectric body material such as Bi layer compound, tungsten bronze structure compound or the like. The electrode layer forming the electroacoustic conversion element 3 is composed of, for example, silver or palladium-containing alloy and this alloy that contains ceramic component and glass component.

Such electroacoustic conversion element 3 can be produced by the following method, for example. First, binder, dispersant, plasticizer and solvent are added to the powdered piezoelectric material, and they are mixed to form a slurry. The obtained slurry is molded into a sheet-like shape to form a green sheet. Next, a conductor paste is printed on the green sheet to form an electrode layer pattern, and the green sheets on which this electrode layer pattern is formed are laminated to form a molded laminate. After that, the molded laminate is degreased, burned and cut into a predetermined dimension to obtain a laminate. Next, a conductor paste to form a surface electrode is printed and burned at a predetermined temperature, then the piezoelectric body layer is polarized by applying DC voltage through the electrode layer. As a result of this, the electroacoustic conversion element 3 can be obtained.

The electroacoustic conversion element 3 is provided on the vibrator 8 via the joining element 7. The joining element 7 is in the form of a film and has a thickness larger than the amplitude of the bending vibration of the electroacoustic conversion element 3. Also, the joining element 7 is formed of a material that is softer and deformable than the extension 2a, and has an elasticity and a rigidity such as Young's modulus, rigidity modulus, bulk modulus or the like smaller than the extension 2a. That is, the joining element 7 is deformable than the extension 2a. It should be noted that the joining element 7 is provided so that it surrounds whole circumference of the electroacoustic conversion element 3. The joining element 7 is provided so that it surrounds the whole circumference of the electroacoustic conversion element 3, and as a result of this, the connection strength between the electroacoustic conversion element 3 and the vibrator 8 can be improved, which prevents the electroacoustic conversion element 3 from being detached from the vibrator 8 easily. Furthermore, the vibration of the electroacoustic conversion element 3 can be transmitted to the vibrator 8 efficiently.

Figure 5:
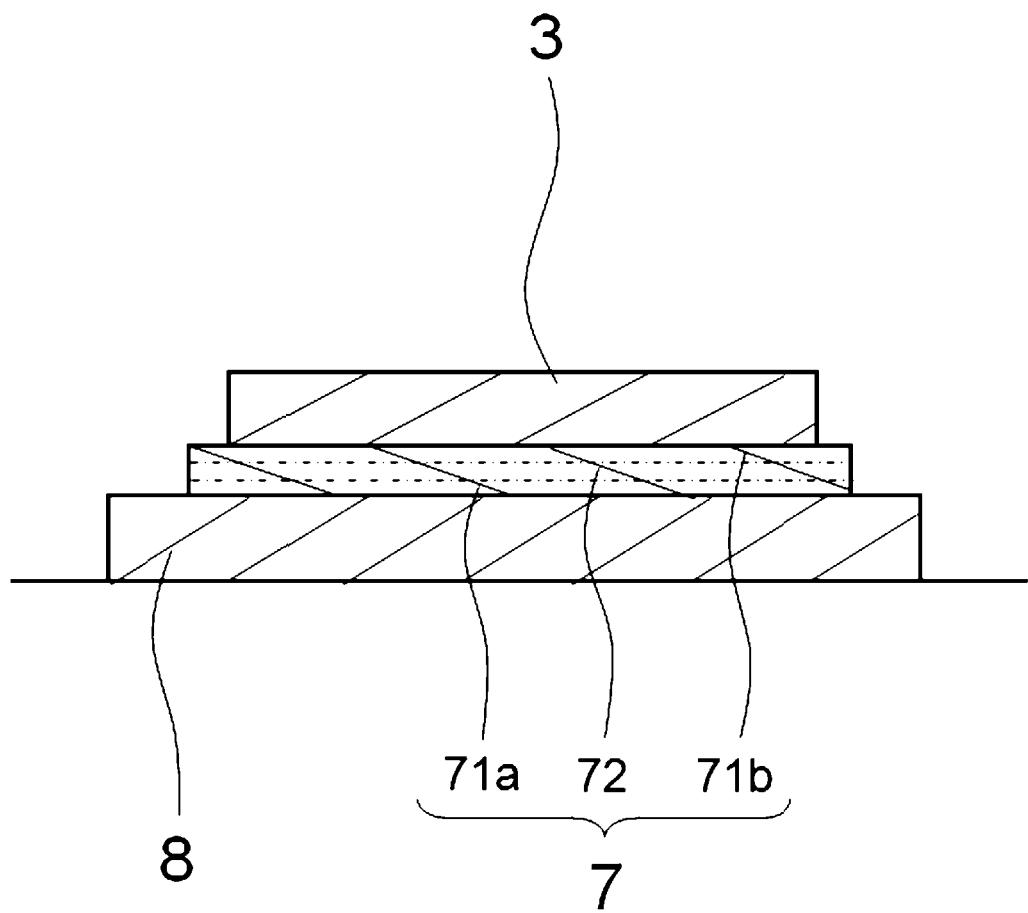
FIG. 5 is a cross-sectional view of a vibrator, a joining element and an electroacoustic conversion element forming a transmission element.

As illustrated in FIG. 5, the joining element 7 has a three-layered structure formed of two-layered adhesive layers 71a and 71b and a base layer 72 disposed therebetween. The lower face (adhesive layer 71a) of the joining element 7 is fixed entirely on the upper face of the vibrator 8 and the upper face (adhesive layer 71b) of the joining element 7 is fixed entirely on the lower face of the electroacoustic conversion element 3.

The adhesive layers 71a and 71b are formed of a viscoelastic body, and its thickness is set, for example, to 10 μm or more and 30 μm or less. The viscoelastic body that forms the adhesive layers 71a and 71b is composed of polymer material such as, for example, acrylic resin, silicon, urethane rubber or the like.

The base layer 72 has a rigidity higher than the adhesive layers 71a and 71b, and its thickness is set, for example, to 50 μm or more and 200 μm or less. The base layer 72 can be formed by preferably using a resin such as polyester or the like. For example, it is desirable to form the base layer 72 of viscoelastic body that forms the adhesive layers 71*a* and 71*b* and nonwoven fabric.

It is also desirable to form the base layer 72 of a material formed of nonwoven fabric and adhesive material, more particularly, of nonwoven fabric impregnated with adhesive material. Furthermore, in the entire thickness direction (direction from one of the two-layered adhesive layers 71*a* and 71*b* toward the other) of the base layer 72, it is desirable to form at least a part thereof of a viscoelastic body. As a result of this, both of an effect of alleviating the thermal stress acting between the vibrator 8 and the electroacoustic conversion element 3 and an effect of transmitting the vibration of the electroacoustic conversion element 3 to the vibrator 8 can be improved.

The acoustic vibration generated from the electroacoustic conversion element 3 is transmitted to the transmission element 4. When the transmission element 4 is applied to the ear, sound can be transmitted satisfactory to the inner ear via a cartilage (sound through tragus). More specifically, a part thereof abuts the vicinity of the tragus 40 while the barrel 2 is fit into the ear canal and transmits the acoustic vibration to the cartilage and the skin in the vicinity of the tragus 40.

The transmission element 4 is provided on the side of the barrel 2. It is a cover element that surrounds the extension 2*a*, and has a built-in electroacoustic conversion element 3. It should be noted that the transmission element 4 is coated with a resin such as epoxy resin, acrylic resin, silicon, urethane rubber or the like. Furthermore, the position of the transmission element 4 is adjusted and set in accordance with the shape of the ear of the user.

An electrical wiring 9 through which a signal to control the electroacoustic conversion element 3 is transmitted is connected to the transmission element 4. Then, one end of the electrical wiring 9 is connected to the transmission element 4. The other end of the electrical wiring 9 is electrically connected to the electrical circuit that controls the electroacoustic conversion element 3 and the power supply that supplies power to the electroacoustic conversion element 3. It should be noted that the electrical wiring 9 is connected to the wire that is electrically connected to the electroacoustic conversion element 3.

The vibration element 5 is provided on the inner wall of the barrel 2 via the adhesive material. The vibration element 5 can vibrate in reaction to the acoustic vibration from the electroacoustic conversion element 3. The vibration of the electroacoustic conversion element 3 is transmitted to the extension 2*a* and to the fitting element 12 via the extension 2*a*, and causes the vibration element 5 located on the inner wall of the barrel 2 to vibrate. The vibration element 5 is shaped so that it fits into the through port T and has the size similar to the inner diameter of the barrel 2. The vibration element 5 is set to have a diameter of 3 mm or more and 15 mm or less and a thickness of 5 mm or more and 30 mm or less.

The vibration element 5 is also provided closer to either one side or the other side of the barrel 2. When the side of the barrel 2 provided with the vibration element 5 is fit into the ear canal, the vibration of the vibration element 5 causes the air in the through port T of the barrel 2 to vibrate, and the air-conducted sound can cause the eardrum in the ear canal to vibrate. It should be noted that the vibration element 5 is formed of a vibration film such as, for example, carbon, liquid crystal polymer film, carbon nanotube or the like. The vibration element 5 may be formed in a mesh shape to allow the external sound to be transmitted to the eardrum easily.

Furthermore, the external sound causes the air inside the through port T of the barrel 2 to vibrate and further causes the vibration element 5 to further vibrate. The vibration of the vibration element 5 then causes the air inside the through port T of the barrel 2 to vibrate, and the air-conducted sound can cause the eardrum in the ear canal to vibrate. It should be noted that, although one end of the barrel 2 where the vibration element 5 is placed closer than the other end is fit into the ear canal when used, the other end of the barrel 2 may be fit into the ear canal for acoustic adjustment.

When one end of the barrel 2 is fit into the ear canal, the biosensor 30 is inserted into the ear canal. When one end of the barrel 2 is fit into the ear canal, the biosensor 30 is provided on the side of the barrel 2 facing the surface of the ear canal. FIG. 3 is a diagram illustrating one example of arrangement of the biosensor 30 in the earphone 1. FIG. 3 is a cross-sectional view of the schematic diagram of the earphone illustrated in FIG. 2 in XZ plane, which is viewed from the minus Y direction to the plus Y direction in FIG. 2. For example, as illustrated in FIG. 3, the earphone 1 has the biosensor 30 on the side opposite the transmission element 4 of the barrel 2. As a result of this, when a part of the barrel 2 is inserted into the left ear of the user, the biosensor 30 contacts the upper portion of the ear canal of the left ear and thus can obtain the biological information of the user on the contact part. The biosensor 30 is positioned away from the electroacoustic conversion element 3 in the earphone 1, and as a result, the biosensor 30 is less likely to be affected by the acoustic vibration and can measure the biological information more accurately.

It should be noted that the above mentioned arrangement of the biosensor 30 is one example, and it can be disposed on the other positions that contact the surface of the ear canal. The biosensor 30 may be provided on the side in the vicinity of the transmission element 4 of the barrel 2 or on the face of the transmission element 4 being in contact with the tragus 40. The biosensor 30 does not always have to be in contact with the measuring object site, it only has to be positioned facing the measuring object site.

The biosensor 30 obtains, for example, the pulse wave as the biological information of the user. The biosensor 30 for obtaining the pulse wave has, for example, a light emitting element and a light receiving element. The light emitting element includes, for example, LED (Light emitting diode) or the like. The light receiving element includes, for example, PT (Phototransistor), PD (Photodiode) or the like. The biosensor 30 for measuring the pulse wave measures the pulse wave data by irradiating the light from the light emitting element to the point of the user where the pulse wave data is measured and receiving the light reflected by the light receiving element. When measuring is made by the light as above mentioned manner, the biosensor 30 does not always have to be in contact with the ear canal.

The biosensor 30 is electrically connected to the electrical wiring 9 via the electrical wiring. The electrical wiring of the biosensor 30 is provided inside the barrel 2 and inside the transmission element 4, for example. The biological information obtained by the biosensor 30 is subjected, as an electrical signal, to the arithmetic processing by the external sensor controller of the earphone 1 via the electrical wiring 9.

The earphone 1 provided with the biosensor 30 can measure the biological information by various methods. The method of measuring the biological information is not limited to the above described method, and other methods may be used. Although the measuring method by light is described for the case where a pulse wave sensor is provided as a biosensor 30, a measuring method by an electrode or by an acceleration sensor or the like may be used.

Although a method of measuring a pulse wave as the biological information has been described in the above mentioned embodiment, the biological information is not limited to the pulse wave. The biological information may be the information relating, for example, to any other living body such as, for example, the body temperature, the blood oxygen level, the blood flow or the like of the user. For example, the sensor controller may detect the fluctuation of the peak interval of pulse waves by using the pulse wave information obtained by the biosensor to determine the condition of autonomic nerve.

The hooking element 6 is placed in the auricle and is positioned between the back side of the auricle and the temporal region. The hooking element 6 is formed to conform to the shape of the auricle, and the hooking element 6 formed to conform to the shape and size of the user's ear is used. The part of the hooking element 6 being in contact with the base of the auricle curves along the shape of the base of the auricle. The hooking element 6 can be provided on the back side of the ear, which allows most of the hooking element 6 to be hidden behind the ear. It should be noted that the surface of the hooking element 6 may be provided with concaves and convexes. Concaves and convexes may reduce the part being in contact with the ear of the user, which prevents the ear canal from getting steamed, and as a result of this, discomfort feeling can be reduced.

The hooking element 6 is formed of an elastically deformable resin, and the surface thereof is covered with a coating material. The coating material is epoxy resin, acrylic resin, silicon, urethane rubber or the like, and is formed of a material that does not adversely affect the human body. The surface of the hooking element 6 is coated with a coating material, which allows the friction with the ear to be reduced when it is placed in the ear and allows the hooking element 6 to be used for a long period of time while being fit into the ear.

One end of the hooking element 6 extends to the ear lobe side. The other end of the hooking element 6 extends to the front side of the auricle. The other end of the hooking element 6 is provided with the transmission element 4 having a built-in electroacoustic conversion element 3.

In the earphone 1 according to this embodiment, a part of the transmission element 4 positioned outside the ear canal abuts the tragus 40 while the barrel 2 is used by fitting into the ear canal. The barrel 2 is fit into the ear canal and as a result it is hardly detached due to vertical motion of the user, thus can be kept fixed into the auricle satisfactory. Compared with the structure in which the barrel 2 itself vibrates a lot, the barrel 2 itself does not vibrate a lot, and potential to gradually fall out due to friction with the surface of the ear canal can be reduced. Furthermore, the electroacoustic conversion element 3 is provided in the transmission element 4 being in contact with the tragus 40 and the transmission element 4 itself is vibrated, and as a result of this, a structure causing the barrel 2 to be less vibrated can be realized.

In the earphone 1 according to this embodiment 1, the transmission element 4 abuts the tragus 40 when the earphone 1 is used while the hooking element 6 is hooked to the ear and further the barrel 2 is fit into the ear canal, and as a result of this, the earphone 1 can continue to be fixed to the auricle satisfactory. Compared with the structure in which the barrel 2 is merely fit into the ear canal, the structure in which the hooking element 6 hooked to the auricle is provided and further the barrel 2 is fit into the ear canal may prevent the earphone 1 from coming off from the auricle easily.

Furthermore, the barrel 2 is provided with the through port T, thus one can hear the ambient sound without being his/her ear canal blocked completely by the barrel 2, and can listen to the music and enjoy it while hearing the ambient sound in condition that the barrel 2 is fit into ear canal. Since the barrel 2 is provided with the through port T, the user of the earphone 1 has less feeling of occlusion caused by a blocked ear canal, and furthermore can listen to the ambient sound.

A battery or an electrical circuit may also be provided in the hooking element 6 which is hooked to the ear. When a battery or an electrical circuit power source is provided in the hooking element 6, there is no more need to extend the wiring from the external power supply or the like, and the user can move freely, allowing for easy use of the earphone 1.

It is preferable to use a piezoelectric element as the electroacoustic conversion element 3. When a piezoelectric element is used, unlike a bone conduction speaker, less acoustic vibration is generated by the piezoelectric element. Thus, even if the electroacoustic conversion element 3 is disposed in the vicinity of the tragus 40, it does not vibrate the user face excessively, causing the skull to vibrate less. As a result of this, there is a little concern about a headache of the user when he/she uses the earphone 1 for a long period of time, thus the user can use the earphone comfortably for a long period of time.

A part of the earphone 1 is provided with the biosensor 30, and as a result, the user can obtain the biological information unintentionally. The transmission element 4 has a built-in electroacoustic conversion element 3, thus it is less likely that the earphone 1 moves out of its position in the ear canal due to vibration of the electroacoustic conversion element 3, allowing the measuring object site of the biological information and the biosensor 30 to be less fluctuated. As a result of this, noise of the biological information measured by using the biosensor 30 is reduced, and the biological information of the user can be measured more accurately. The biosensor 30 is positioned on a part of the barrel 2 that is away from the electroacoustic conversion element 3, and as a result, it is less affected by the vibration, and thus can measure the biological information of the user more accurately.

It should be noted that this disclosure is not limited to the above mentioned embodiment, and may be modified or changed in the scope without departing from the spirit of this disclosure. Variations according to the embodiment of this disclosure are described below. It should be noted that the same parts of the earphone according to the variations of this disclosure are indicated by the same symbols as those of the earphone according to the embodiment of this disclosure and the explanation thereof will be omitted appropriately.

Variation 1

Figure 6:
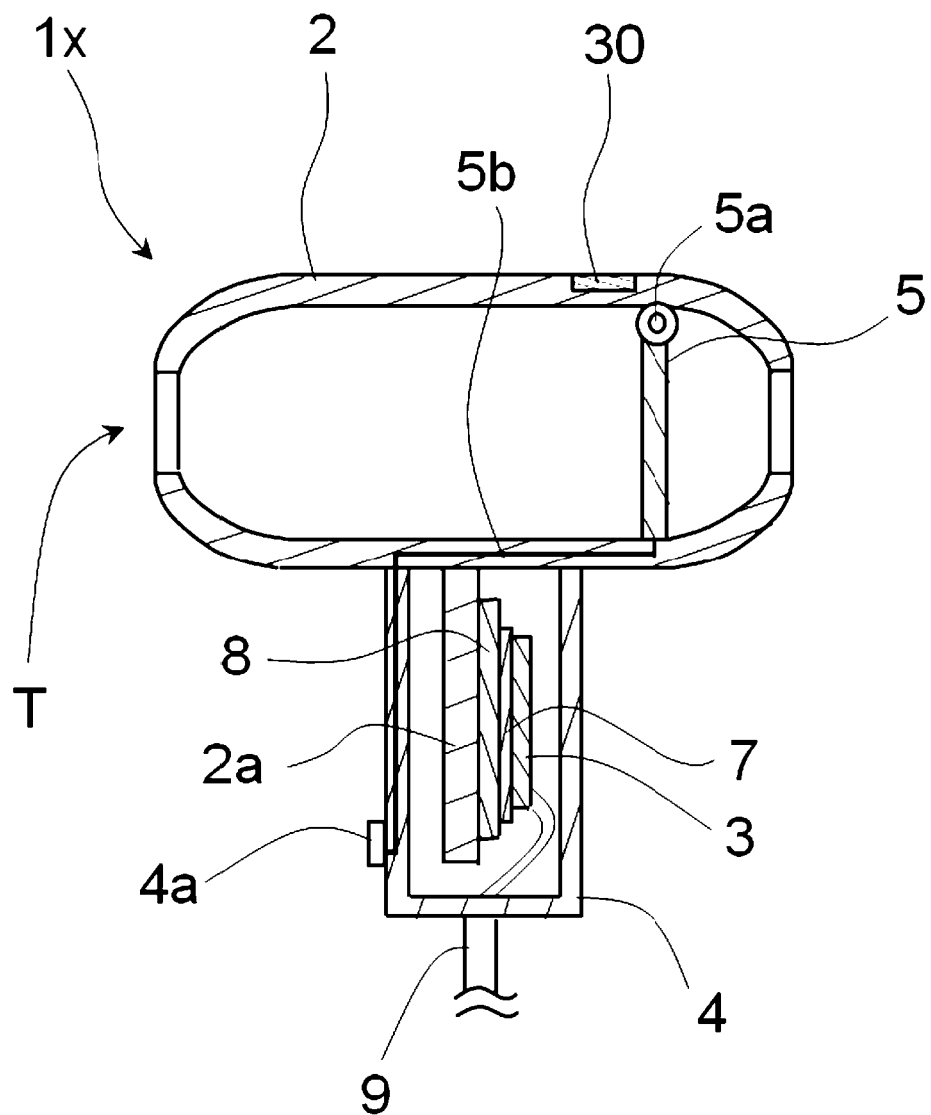
FIG. 6 is a cross-sectional view of an earphone according to Variation 1 corresponding to FIG. 3.
Figure 7:
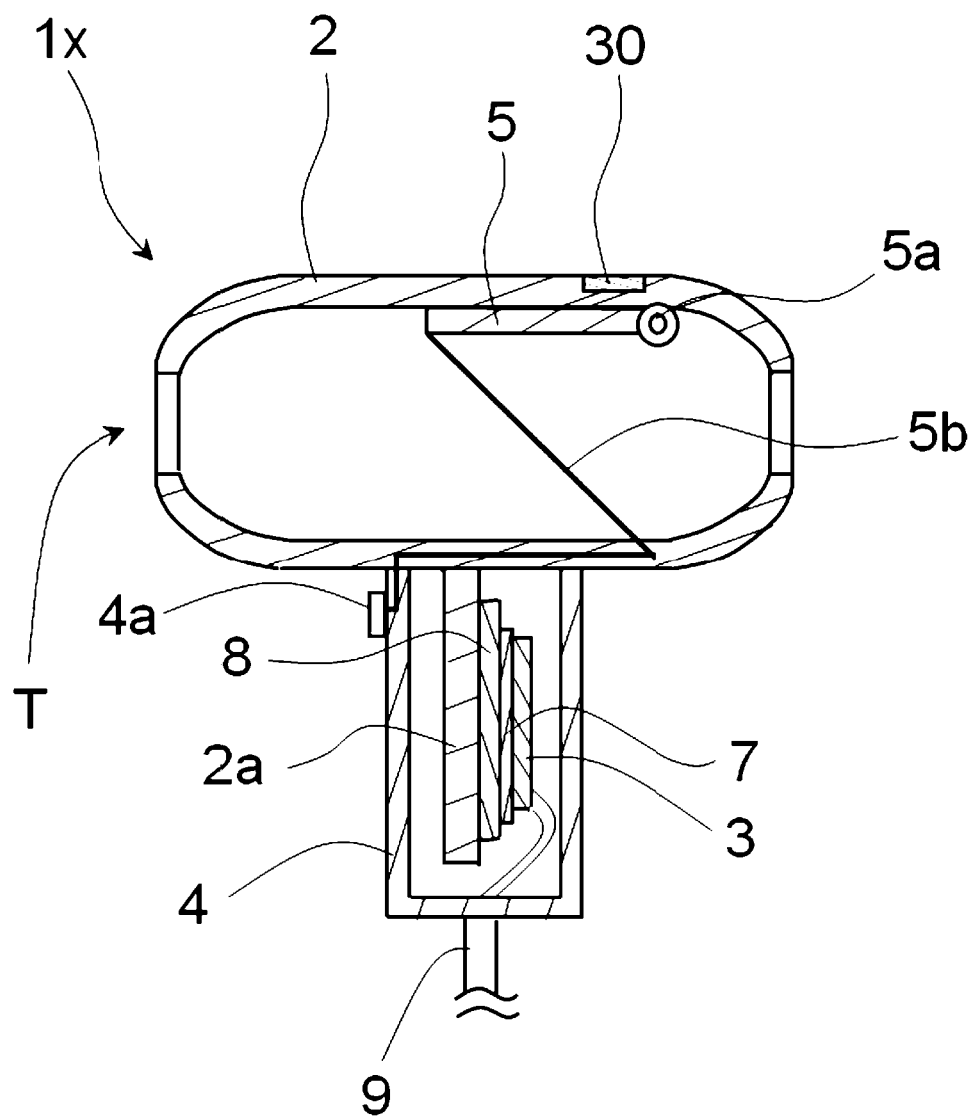
FIG. 7 is a cross-sectional view of the earphone according to Variation 1 corresponding to FIG. 3.

FIGS. 6 and 7 are cross-sectional views of an earphone 1x according to Variation 1, and correspond to the cross section in FIG. 3. FIG. 6 illustrates a state where the vibration element 5 closes the through port T of the barrel 2. FIG. 7 illustrates a state where the vibration element 5 opens the through port T of the barrel 2. In the above mentioned embodiment, although the vibration element 5 is fixed to the inner wall of the barrel 2, the state is not limited thereto. The earphone 1x according to Variation 1 is provided openably/closeably on the inner wall of the barrel 2.

In the earphone 1x according to Variation 1, a button 4a which is slidable relative to the outer face of the transmission element 4 is provided on the transmission element 4. One end of the vibration element 5 is openable/closable via a hinge 5a, for example, and a wire 5b such as a string or a string wire or the like is attached to the other end of the vibration element 5. Furthermore, the wire 5b is connected to the button 4a, and the wire 5b is pulled as the button 4a moves, and the vibration element 5 opens/closes about the hinge 5a as an axis. It should be noted that the vibration element 5 is applied with a force so that the opening state is kept in the direction of opening the through port T of the barrel 2 by a spring.

The loudness and the sound quality of the air-conducted sound transmitted to the eardrum can be adjusted by adjusting the opening/closing state of the vibration element 5 by the user. The ambient sound which passes through the through port T of the barrel 2 and is changed by the vibration element 5 is allowed to be adjustable, and as a result, the user can listen to the ambient sound or the sound converted to the acoustic vibration by the electroacoustic conversion element 3 with concentration, thus the freedom of specification can be improved. It should be noted that, in Variation 1, the button 4a has a slide-type structure. However, the structure is not limited thereto, and the opening/closing state of the vibration element 5 may be adjusted according to the pressing period of the button, for example.

Variation 2

Figure 8:
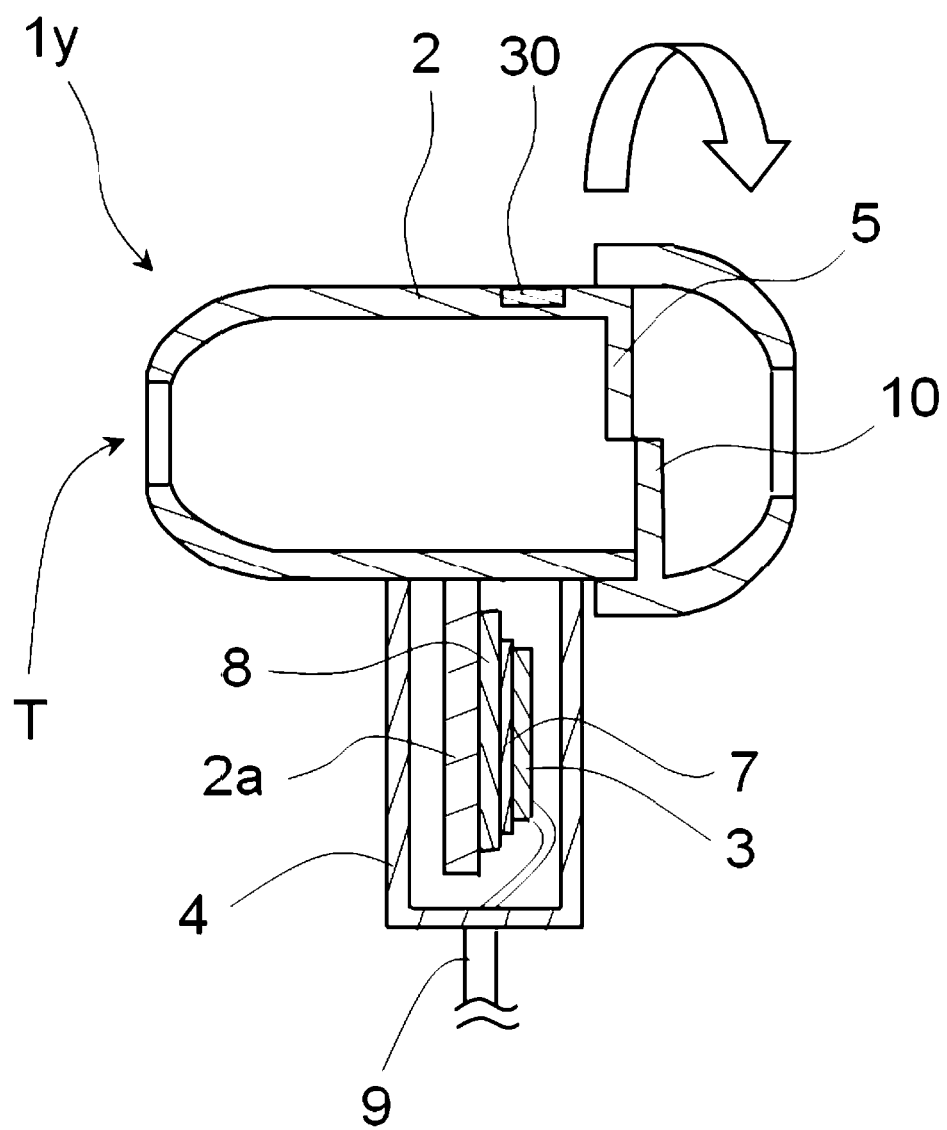
FIG. 8 is a cross-sectional view of an earphone according to Variation 2 corresponding to FIG. 3.
Figure 9:
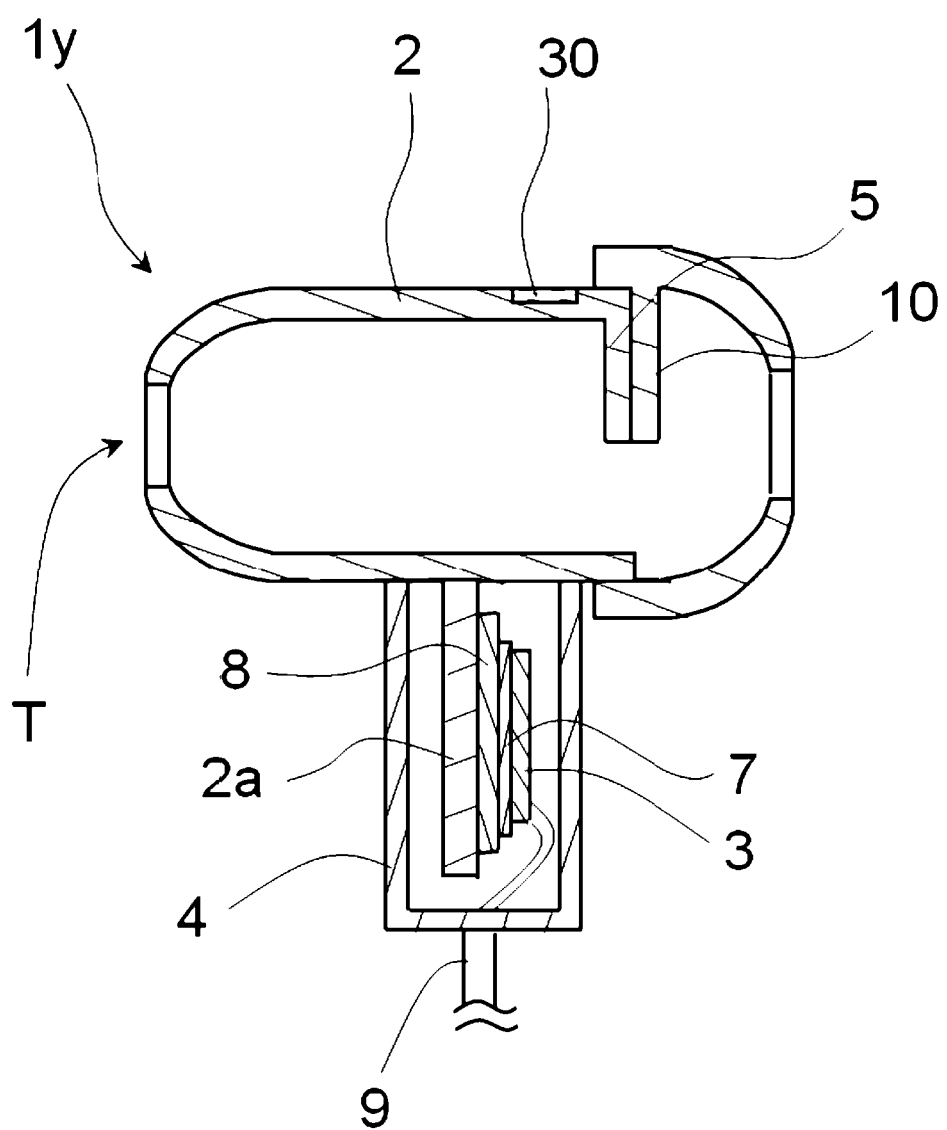
FIG. 9 is a cross-sectional view of the earphone according to Variation 2 corresponding to FIG. 3.

FIGS. 8 and 9 are cross-sectional views of an earphone 1y according to Variation 2, and correspond to the cross section in FIG. 3. FIGS. 8 and 9 illustrate a structure in which one end of the barrel 2 is rotatable around the axis along the penetrating direction of the through port T. FIG. 8 illustrates a state where, instead of the vibration element 5, an adjusting plate 10 closes the through port T of the barrel 2. FIG. 9 illustrates a state where the adjusting plate 10 opens the through port T of the barrel 2. In the above mentioned Variation 1, although the vibration element 5 itself opens/closes, the structure is not limited thereto. The earphone 1y according to Variation 2 is provided with, instead of one piece of disc-shaped vibration element 5, a semicircular vibration element 5 and a semicircular adjusting plate 10. The adjusting plate 10 has the same function as the vibration element 5, is a part of the vibration element 5, and can vibrate in reaction to the acoustic vibration from the electroacoustic conversion element 3.

In the earphone 1y according to Variation 2, one end of the barrel 2 is rotatable around the axis of the through port T. The inner wall of one end of the rotatable barrel 2 is provided with a semicircular plate, and the inner wall of the region sandwiched between both ends of the fixed barrel 2 is provided with a semicircular plate. Then both of them are used as an adjusting plate 10. One end of the barrel 2 rotates and as a result one semicircular plate rotates. Then the region overlapped with the other semicircular plate is adjusted, and as a result, the ambient sound transmitted into the through port T of the barrel 2 can be adjusted. It should be noted that the adjusting plate 10 is formed of the same material as that of the vibration element 5.

Figure 10:
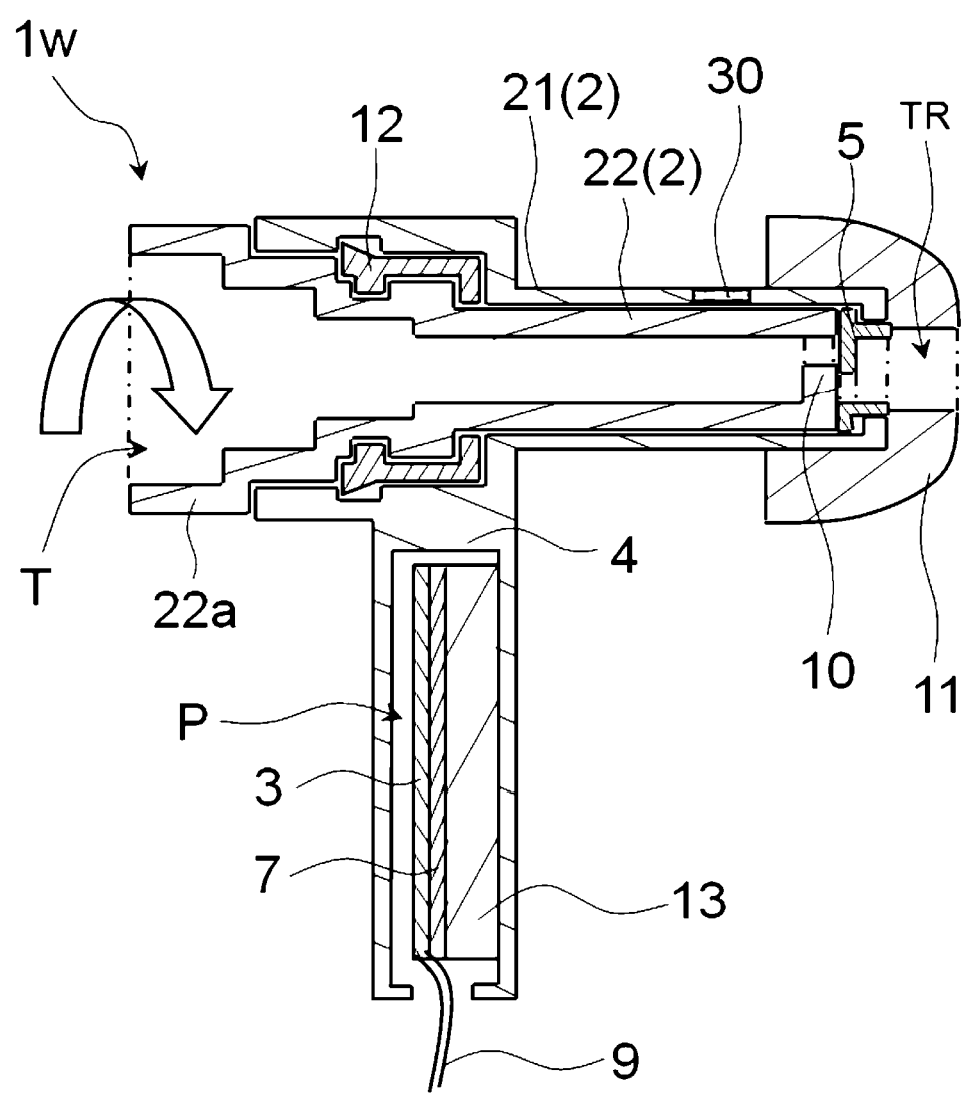
FIG. 10 is a cross-sectional view of a concrete example of the earphone according to Variation 2 corresponding to FIG. 8.
Figure 11:
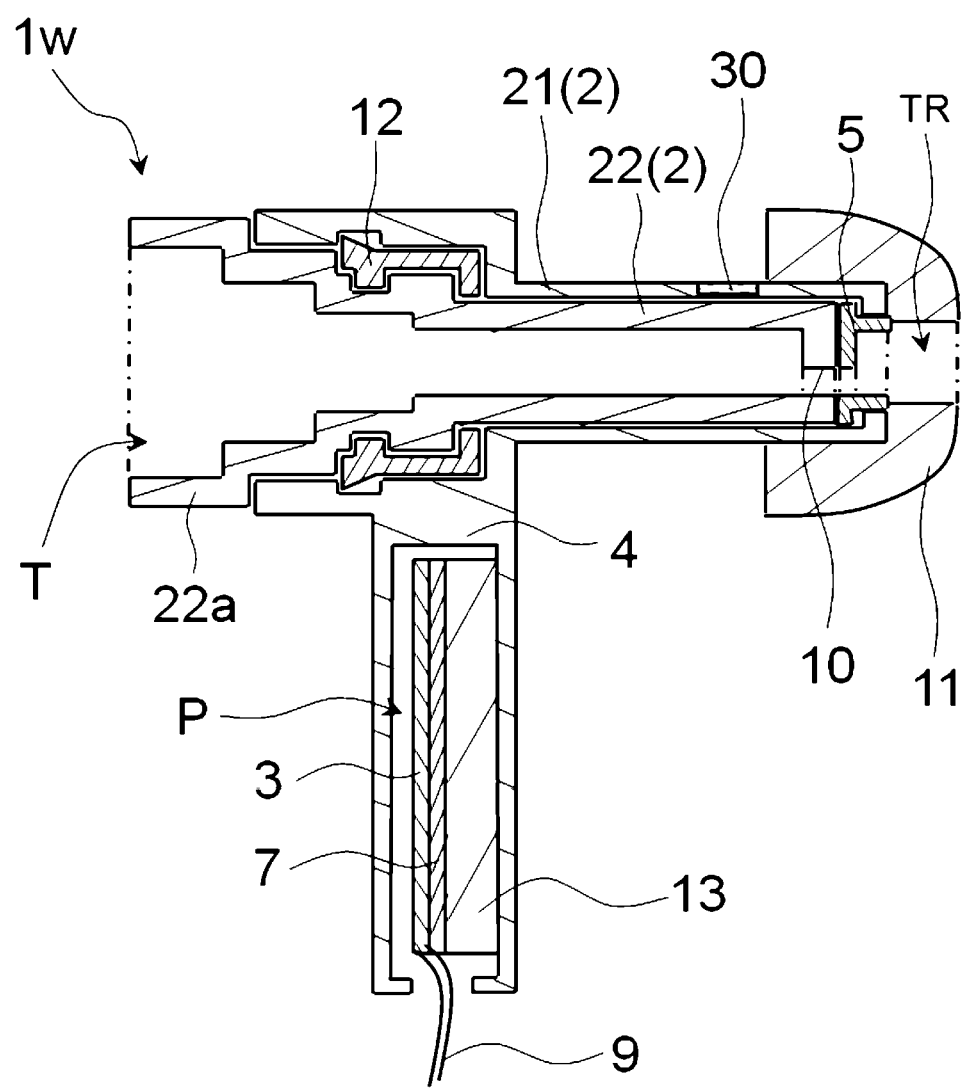
FIG. 11 is a cross-sectional view of a concrete example of the earphone according to Variation 2 corresponding to FIG. 9.

FIGS. 10 and 11 are cross-sectional views of an earphone 1w which embodies the earphone 1y according to Variation 2. FIGS. 10 and 11 illustrate a structure in which one end of the barrel 2 is rotatable around the axis along the penetrating direction of the through port T. FIG. 10 illustrates a state where the space on the through port T side and the space on the eardrum side are separated by the vibration element 5 and the adjusting plate 10. FIG. 11 illustrates a state where the space on the through port T side and the space on the eardrum side are connected by rotating the adjusting plate 10 around the axis along the penetrating direction of the through port T. That is, the vibration element 5 (adjusting plate 10) is provided so that it separates the space inside the barrel 2, and the adjusting plate 10 as a part of the vibration element 5 can move so that it separates or connects the space inside the barrel 2.

In this concrete example, the barrel 2 is divided into two elements, and both of them can move relative to each other. An ear cushion 11 is provided to cover a part on one end of the barrel 2 being in contact with the inner ear of the auricle. The ear cushion 11 is formed of a material that does not damage the auricle of the user, such as, for example, urethane, silicon, rubber or the like. In the ear cushion 11, an opening port TR that can connect the space on the eardrum side and the space inside the barrel 2 is formed along the penetrating direction of the through port T. The opening diameter of the opening port TR is set to 5 mm or more and 10 mm or less, for example.

Here, in the barrel 2, the barrel 2 coupled to the transmission element 4 is a first barrel 21, and the barrel 2 provided by being inserted into the first barrel 21 is a second barrel 22. The second barrel 22 is provided so that it does not come off from inside the first barrel 21 via a fitting element 12 provided inside the first barrel 21. A part of the fitting element 12 is mounted along the outer edge of the barrel 2. The fitting element 12 is fit into the groove provided on the inner wall of the first barrel 21 and is also fit into the groove provided on the peripheral surface of the second barrel 22. The second barrel 22 can be moved relative to the first barrel 21 via the fitting element 12. The fitting element 12 is formed of resin or the like, for example.

One end 22a of the second barrel 22 where the ear cushion 11 is not provided projects outward from the space inside the first barrel 21. The projection 22a can be held between one's fingers. The projection 22a can be rotated around the axis along the penetrating direction of the through port T. That is, the other end of the barrel 2 is rotatable around the axis along the penetrating direction of the through port T of the barrel 2, and as a result, the adjusting plate 10, which is a part of the vibration element 5, moves when the other end of the barrel 2 rotates.

As illustrated in FIG. 10 or FIG. 11, a sponge 13 is provided in the transmission element 4. The electroacoustic conversion element 3 is connected to the sponge 13 via the joining element 7. In the electroacoustic conversion element 3, the face not connected to the joining element 7 is spaced apart from the inner wall of the transmission element 4. A gap P is provided between the inner wall of the transmission element 4 and the electroacoustic conversion element 3. The sponge 13 is formed of urethane sponge, polyethylene sponge or the like. The sponge 13 is large enough to mount the electroacoustic conversion element 3, and is set to a rectangular parallelepiped shape having a length of 10 mm or more and 40 mm or less, a width of 1 mm or more and 30 mm or less and a thickness of 0.3 mm or more and 5 mm or less, for example.

The electroacoustic conversion element 3 is mounted on the sponge 13 via the joining element 7 and one principal surface of the electroacoustic conversion element 3 is exposed in the gap P, and as a result, the electroacoustic conversion element 3 is less restricted by the surrounding elements. Since one principal surface of the electroacoustic conversion element 3 is exposed in the gap P and the other principal surface of the electroacoustic conversion element 3 is adhered to the sponge 13 via the joining element 7 which is more deformable than the transmission element 4 itself, the electroacoustic conversion element 3 is in the state of being deformable in response to an electrical signal. The electroacoustic conversion element 3 vibrates a lot in response to an electrical signal to increase the vibration sound. The louder the vibration sound becomes, the easier the sound transmission to the eardrum via the sound transmission element 4 or the vibration element 5 becomes.

The earphones 1y and 1w according to this variation are provided so that the adjusting plate 10 can move while each of them is fit into the ear canal. Then, the space on the through port T side and the space on the eardrum side can be separated or connected by the vibration element 5 and the adjusting plate 10.

In the state where the space on the through port T side and the space on the eardrum side are separated while the ear cushion 11 is fit into the ear canal, the acoustic vibration generated by the transmission element 4 is transmitted to the adjusting plate 10 and the vibration element 5 via the barrel 2 to cause the adjusting plate 10 and the vibration element 5 to vibrate. The air-conducted sound can be generated by the vibration element 5 and transmitted to the eardrum in the ear canal. In the state where the ear cushion 11 is fit into the ear canal, a small clearance is provided between the eardrum and the vibration element 5, and the clearance allows the sound to be confined between the eardrum and the vibration element 5, which causes resonance to occur easily, and as a result, low frequency sound can be generated. In the earphone 1w according to this variation, the vibration element 5 is provided to block the eardrum, and a small clearance is created between the eardrum and the vibration element 5, which causes low frequency sound of 1 kHz or less to resonate easily.

Further, in the state where the adjusting plate 10 is moved and the space on the through port T side and the space on the eardrum side are connected, the ambient sound can be transmitted to the eardrum through the opening port TR of the ear cushion 11 connected to the through port T as a space inside the barrel 2. As a result of this, when the earphone 1w is used, both the air-conducted sound by the acoustic vibration and the ambient sound are transmitted to the eardrum, thus sound can be transmitted to the user.

In the earphone 1w according to this variation, it is further desirable that a part of the transmission element 4 located outside the ear canal abuts the tragus 40 while the ear cushion 11 is fit into the ear canal. The vibration of the transmission element 4 causes the tragus 40 to vibrate, is transmitted to the cochlea via the cartilage of the ear and is converted to sound. When the vibration of the transmission element 4 is transmitted to the barrel 2 and causes the barrel 2 to vibrate, the transmitted vibration causes the surface of the ear canal to vibrate, and the air-conducted sound is generated on the surface of the ear canal and reaches the eardrum.

When a piezoelectric element is used as the electroacoustic conversion element 3, unlikely the bone conduction speaker, less acoustic vibration is generated by the piezoelectric element. Thus, even if a piezoelectric element is disposed in the vicinity of the tragus 40, the user face does not vibrate excessively, causing the skull to vibrate less. As a result of this, there is a little concern about a headache of the user when he/she uses the earphone 1y and 1w for a long period of time, thus the user can use the earphone comfortably for a long period of time.

Variation 3

Figure 12:
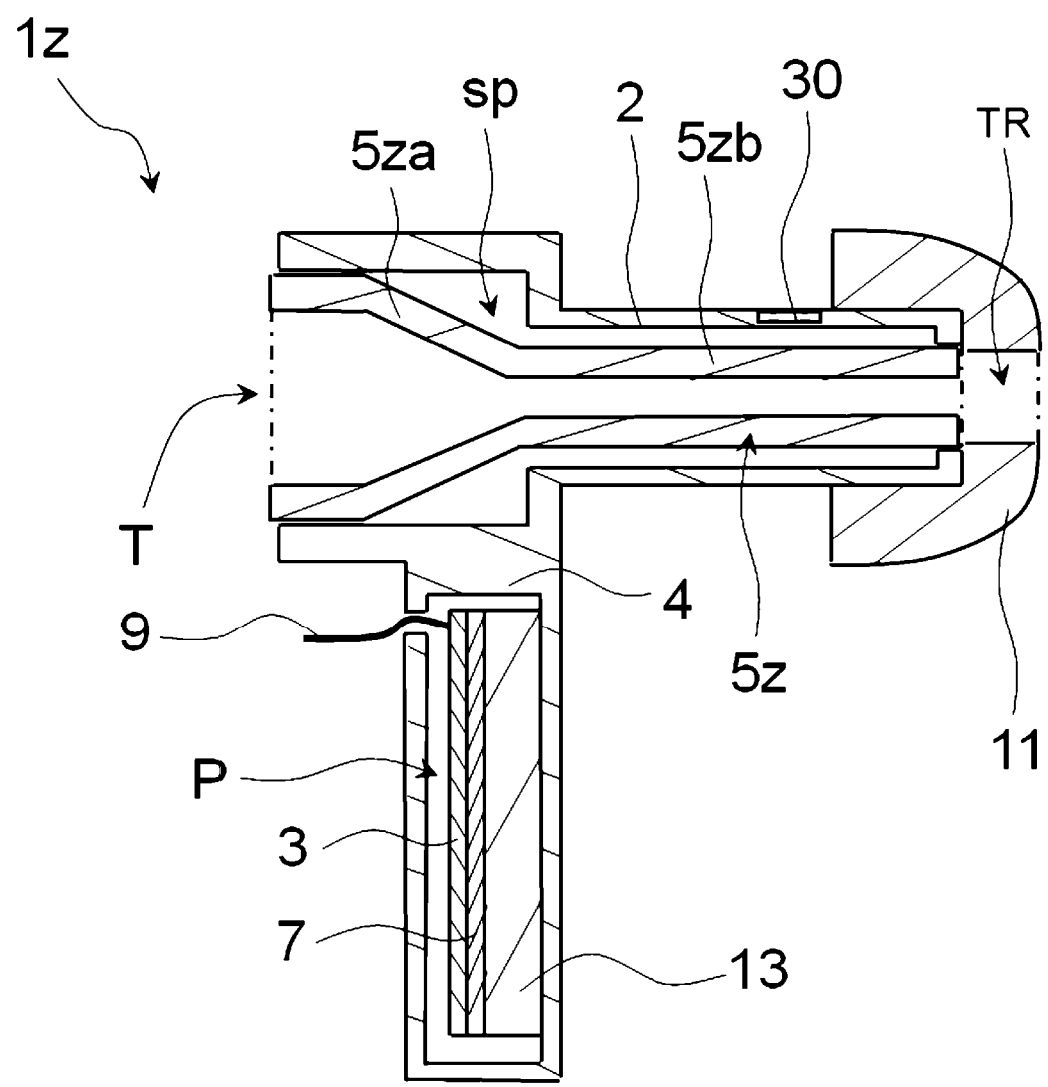
FIG. 12 is a cross-sectional view of an earphone according to Variation 3 corresponding to FIG. 3.

FIG. 12 is a cross-sectional view of the earphone 1z according to Variation 3, and corresponds to the cross section in FIG. 3. In FIG. 12, the vibration element 5z may be formed by combining a hollow triangular pyramid part and a cylindrical part 5zb extending from the vertex of the triangular pyramid part 5za. That is, the vibration element 5z may be a trumpet shape. It should be noted that the inner space of the triangular pyramid part 5za and the inner space of the cylindrical part 5zb are connected.

The vibration element 5z is connected to a part of the inner wall of the barrel 2 via an adhesive material, for example. The vibration element 5z can vibrate in reaction to the acoustic vibration from the electroacoustic conversion element 3. The vibration element 5z is large enough to allow a part of the outer edge of the triangular pyramid part 5za to fit into the through port T, and has the same size as the inner diameter of the barrel 2. The vibration element 5z is set to have an inner diameter of 1 mm or more and 3 mm or less, an outer diameter of 1.5 mm or more and 4.3 mm or less and a length along the barrel 2 is 10 mm or more and 20 mm or less. It should be noted that the vibration element 5z is formed of resin material such as, for example, polycarbonate resin, acrylic resin, polyacetate resin, polyvinyl chloride or the like or metal material such as aluminum, copper, iron or the like.

Figure 13:
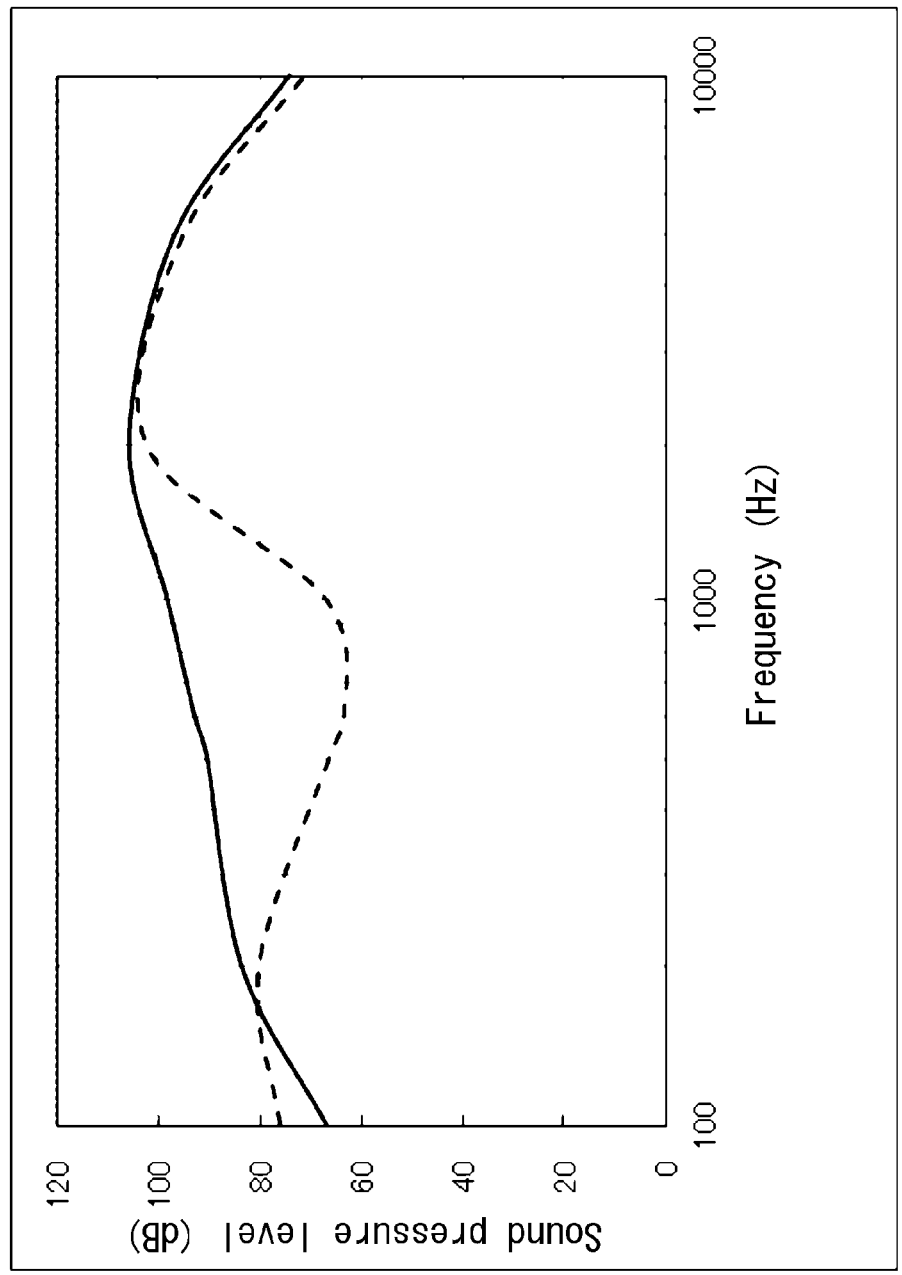
FIG. 13 is an ambient sound evaluation result relating to the earphone according to Variation 3.
Figure 14:
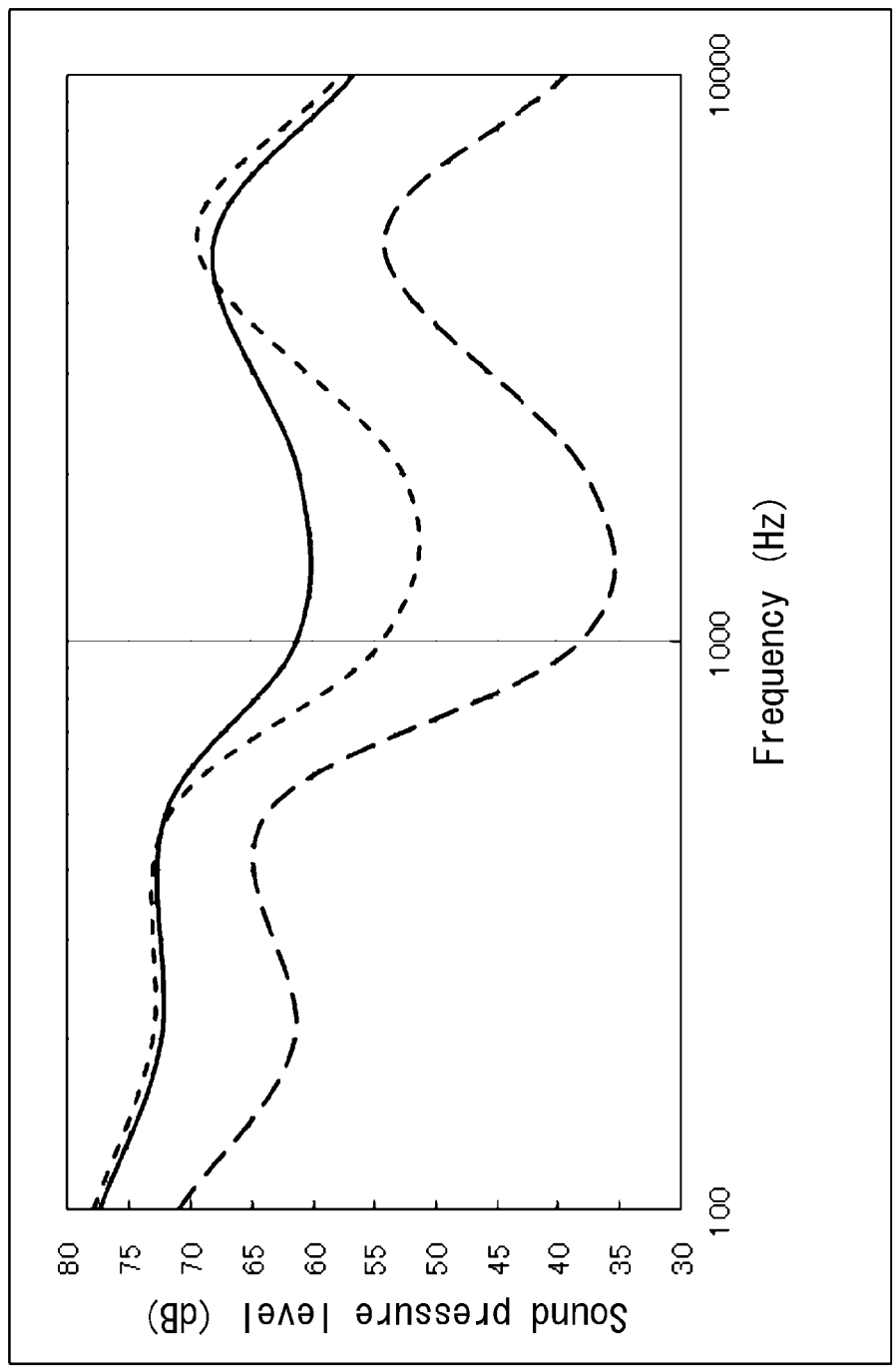
FIG. 14 is an ambient sound evaluation result relating to the earphone according to Variation 3.

FIGS. 13 and 14 illustrate respectively an evaluation result of the sound pressure level characteristics of the listening sound source and the ambient sound relating to the earphone 1z according to Variation 3. For the sound pressure level characteristics of the listening sound source, the earphone is mounted on a dummy head disposed in an anechoic box where reflections of sound are absorbed, and sound wave of each frequency is radiated from the earphone. The sound detected by a capacitor microphone in the dummy head is evaluated as sound of the listening sound source listened to by the user who wears the earphone. It should be noted that each frequency from the earphone is in the range from 100 Hz to 10000 Hz.

On the other hand, the ambient sound evaluation is made by providing a dummy head wearing an earphone in the anechoic box where reflections of sound are absorbed, and sound wave of each frequency is radiated from a speaker in the anechoic box. The sound detected by the capacitor microphone in the dummy head is evaluated as the ambient sound listened to by the user who wears the earphone. It should be noted that each frequency from the earphone is in the range from 100 Hz to 10000 Hz.

FIG. 13 is an earphone 1z according to Variation 3, and illustrates a result of comparison between the case where there is an inner space sp and the case where there is no inner space sp. The case where there is an inner space sp is indicated by a solid line and the other case is indicated by a dashed line.

A part of the barrel 2 is cylindrical, and a part of the vibration element 5z is a triangular pyramid part 5za, and as a result, an inner space sp is formed between the inner wall of the barrel 2 and the side of the triangular pyramid part 5za. As illustrated in FIG. 13, when the inner space sp is provided, the case where there is the inner space sp has a higher sound pressure level than the case where there is no inner space sp in the frequencies from 200 Hz to 2000 Hz. This shows a state where what is called a low frequency sound pressure level is kept high. As a result of this, the earphone 1z according to this variation provided with the inner space sp has excellent sound pressure characteristics in the low frequency range of some hundreds, and sound and music can be listened to clearly. It should be noted that the inner space sp extends also between the cylindrical part of the vibration element 5z and the side of the cylindrical part 5zb.

FIG. 14 illustrates the results of three earphones. The solid line indicates the evaluation result of the earphone 1z according to this variation. The dashed line indicates the earphone that has a through port T, but the shape of its end on the ambient side is a narrow tube. The long dashed line indicates the evaluation result of the closed type earphone that has no through port T and has a closed port.

As illustrated in FIG. 14, the closed type earphone has a low sound pressure level at each frequency, which indicates that the ambient sound is difficult to be listened to. When the user listens to the ambient sound by removing the vibration element 5z from the earphone 1z according to this variation, it is easier for the user to listen to the ambient sound than the closed type earphone. Furthermore, FIG. 14 indicates that the earphone 1z according to this variation has an improved sound pressure level in the frequency range from 500 Hz to 4000 Hz due to provision of the vibration element 5z. As a result of this, compared with the closed type earphone or the earphone that has a through port T, has an end on the ambient side in the shape of a narrow tube and provided with no vibration element 5z, the earphone 1z according to this variation provided with the vibration element 5z allows the user to listen to the ambient sound easily.

Figure 15:
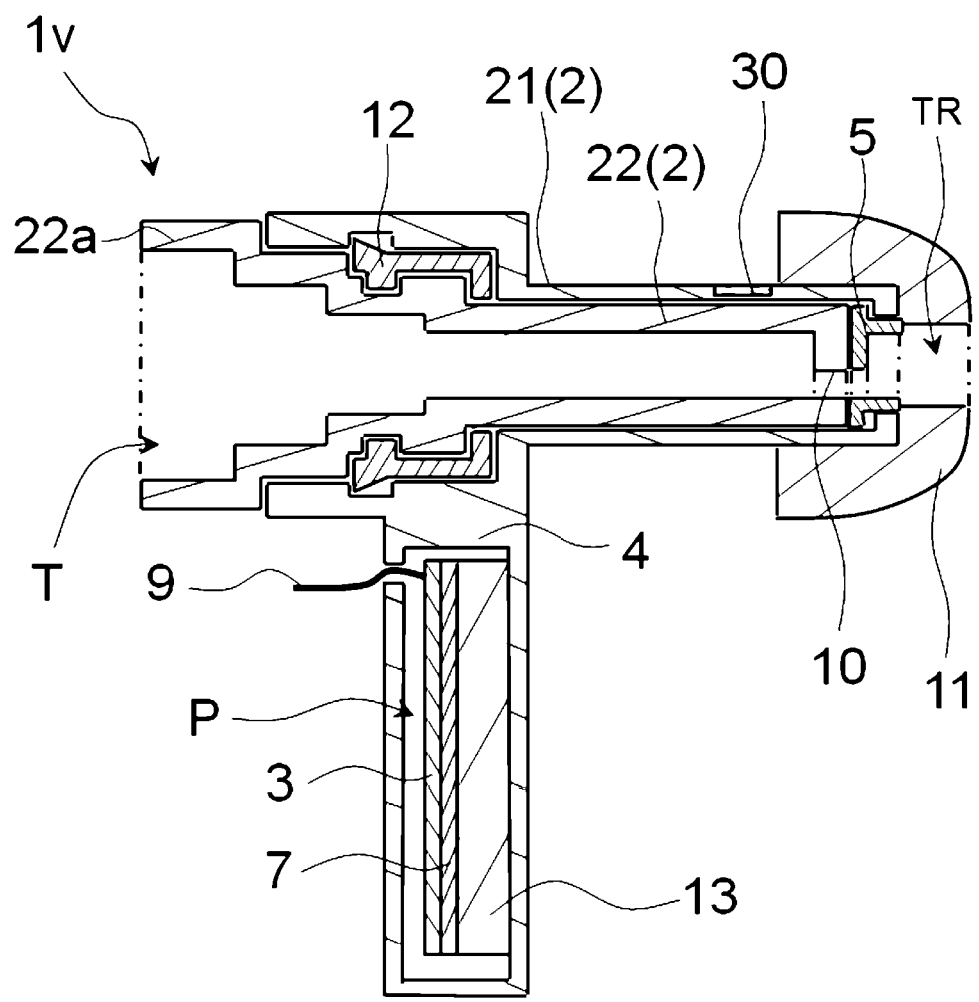
FIG. 15 is a cross-sectional view of a variation of the earphone according to Variation 2 corresponding to FIG. 9.

In this variation, the electrical wiring 9 is drawn around so that it is taken from the base of the transmission element 4. The electrical wiring 9 is connected closer to the barrel 2 relative to the electroacoustic conversion element 3, which allows the vibration of the electroacoustic conversion element 3 to be less inhibited and allows the electroacoustic conversion element 3 to vibrate near the barrel 2. Thus, the acoustic vibration can be transmitted from the transmission element 4 to the barrel 2 efficiently. As a result of it, the sound pressure level can be maintained favorably. It should be noted that, as illustrated in FIG. 15, in the above mentioned embodiment or variations, the electrical wiring 9 may be drawn from the base of the transmission element 4.

According to this variation, the vibration element 5z is provided, and as a result, a state where the ear canal is opened to the ambient is kept and the environmental sound (ambient sound) is allowed to be listened to more easily. Furthermore, the sound pressure level in the low frequency range, which is a problem of the piezoelectric type, is improved in a state where the ear canal is opened to the ambient in which the sound pressure level characteristics in the low frequency range normally declines, and as a result, listening sound source (program voice, speech voice, music or the like) can be listened to clearly.

REFERENCE SIGNS LIST 1, 1x, 1y, 1w, 1z, 1v Earphone
2 Barrel
2a Extension
3 Electroacoustic conversion element
4 Transmission element
4a Button
5, 5z Vibration element
5a Hinge
5za Triangular pyramid part
5zb Cylindrical part
6 Hooking element
7 Joining element
8 Vibrator
9 Electrical wiring
10 Adjusting plate
11 Ear cushion
12 Fitting element
13 Sponge
21 First barrel
22 Second barrel
30 Biosensor
40 Tragus
71a, 71b Adhesive layer

The invention claimed is:

1. An earphone characterized in that it comprises:
a tubular barrel having first and second ends opposite to each other along an axis of the barrel, the first end thereof insertable in an ear canal;
a transmission element that is provided on a part of a side of the barrel between the first and second ends of the barrel, has a part thereof being in contact with a tragus while the barrel is inserted in the ear canal and has a built-in electroacoustic conversion element configured to generate an acoustic vibration in response to an electrical signal;
a vibration element provided on an inner wall of the barrel and configured to vibrate in reaction to the acoustic vibration from the electroacoustic conversion element; and a biosensor, wherein
the transmission element has an extension extending from the side of the barrel to a direction orthogonal to the axis of the barrel, and the electroacoustic conversion element is provided on the extension via a joining element surrounding a whole circumference of a surface of the electroacoustic conversion element along the direction orthogonal to the axis of the barrel.

2. The earphone according to claim 1, wherein the biosensor is provided on the barrel.

3. The earphone according to claim 1, wherein the vibration element is provided closer to either one of the first end or the second end of the barrel.

4. The earphone according to claim 1, wherein the vibration element is provided to separate a space in the barrel, and a part of the vibration element can move to separate and connect the space in the barrel.

5. The earphone according to claim 4, wherein the second end of the barrel is rotatable around an axis along a penetrating direction of a through port of the barrel, and rotation of the second end of the barrel allows a part of the vibration element to move.

6. The earphone according to claim 1, wherein the vibration element has a shape formed by combining a triangular pyramid part having a gap inside thereof and a cylindrical part extending from a vertex of the triangular pyramid part, and an inner space of the triangular pyramid part and an inner space of the cylindrical part are connected.

7. The earphone according to claim 1, wherein the transmission element is provided with an elastically deformable hooking element to be hooked to an auricle.

8. The earphone according to claim 1, wherein the vibration element is attached to the inner circumferential wall of the barrel via a hinge and is configured to move about the hinge to open and close a through port of the barrel.

9. The earphone according to claim 1, wherein the second end of the barrel is rotatable around an axis along a penetrating direction of a through port of the barrel, and rotation of the second end of the barrel allows a part of the vibration element to move to open and close a through port of the barrel according to a rotation angle of the other end of the barrel.

10. The earphone according to claim 1, wherein
the vibration element has a shape formed by combining a triangular pyramid part and a cylindrical part extending from a vertex of the triangular pyramid part, and an inner space of the triangular pyramid part and an inner space of the cylindrical part are connected, and
an inner space is formed between an outer circumferential surface of the cylindrical part and the inner circumferential wall of the barrel over a substantially entire length of the cylindrical part.

* * * * *